(12) United States Patent
Junginger (10) Patent No.: US 10,130,521 B2
(45) Date of Patent: *Nov. 20, 2018

(54) WOUND DRESSING (75) Inventor: Martin Junginger, Hermaringen (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/000,845

(22) PCT Filed: Jul. 1, 2009

(86) PCT No.: PCT/EP2009/004734
§ 371 (c)(1),
(2), (4) Date: Mar. 11, 2011

(87) PCT Pub. No.: WO2010/000451
PCT Pub. Date: Jan. 7, 2010

(65) Prior Publication Data
US 2011/0280926 A1    Nov. 17, 2011

(30) Foreign Application Priority Data
Jul. 3, 2008 (DE) .................. 10 2008 031 183

(51) Int. Cl.
| A61K 9/70 | (2006.01) |
| B32B 37/02 | (2006.01) |
| B32B 37/14 | (2006.01) |
| A61P 17/02 | (2006.01) |
| A61F 13/02 | (2006.01) |
| A61F 13/00 | (2006.01) |

(52) U.S. Cl.
CPC .... A61F 13/0209 (2013.01); A61F 13/00991 (2013.01); A61F 13/025 (2013.01); A61F 13/0213 (2013.01); A61F 13/0223 (2013.01); A61F 13/0289 (2013.01); *A61F 2013/0017* (2013.01); *A61F 2013/0074* (2013.01); *A61F 2013/00217* (2013.01); *A61F 2013/00255* (2013.01); *A61F 2013/00259* (2013.01); *A61F 2013/00604* (2013.01); *A61F 2013/00663* (2013.01); *A61F 2013/00697* (2013.01); *A61F 2013/00727* (2013.01); *A61F 2013/00748* (2013.01); *A61F 2013/00774* (2013.01); *A61F 2013/00863* (2013.01); *A61F 2013/00868* (2013.01); *Y10T 156/10* (2015.01)

(58) Field of Classification Search
None
See application file for complete search history.

(56) References Cited
U.S. PATENT DOCUMENTS

| 3,978,855 A * | 9/1976 | McRae et al. ................. 602/46 |
| 4,393,048 A | 7/1983 | Mason, Jr. |
| 5,064,653 A | 11/1991 | Sessions et al. |
| 5,106,629 A * | 4/1992 | Cartmell ............. A61F 13/0203 424/443 |
| 5,292,777 A * | 3/1994 | DesMarais et al. ............ 521/64 |
| 5,429,589 A * | 7/1995 | Cartmell et al. ................ 602/42 |
| 5,489,262 A | 2/1996 | Cartmell et al. |
| 5,569,207 A * | 10/1996 | Gisselberg et al. ........... 604/175 |
| 5,635,201 A | 6/1997 | Fabo |
| 5,844,013 A | 12/1998 | Kenndoff et al. |
| 6,034,149 A * | 3/2000 | Bleys et al. .................. 521/155 |
| 6,051,747 A | 4/2000 | Lindqvist et al. |
| 6,977,323 B1* | 12/2005 | Swenson ......................... 602/46 |
| 7,943,811 B2* | 5/2011 | Da Silva Macedo, Jr. ..... 602/54 |
| 8,147,857 B2* | 4/2012 | Fugmann et al. ............. 424/409 |
| 2003/0120229 A1 | 6/2003 | De Jong et al. |
| 2004/0122388 A1 | 6/2004 | McCormack et al. |
| 2004/0123590 A1* | 7/2004 | Tabata et al. .................... 60/295 |
| 2004/0153040 A1* | 8/2004 | Martineau et al. .......... 604/304 |
| 2004/0241214 A1 | 12/2004 | Kirkwood |
| 2005/0123590 A1* | 6/2005 | Burton et al. ................. 424/445 |
| 2005/0226917 A1* | 10/2005 | Burton ......................... 424/445 |
| 2006/0149017 A1 | 7/2006 | Graham |
| 2006/0200063 A1 | 9/2006 | Munro et al. |
| 2008/0255493 A1* | 10/2008 | Sigurjonsson et al. ......... 602/44 |
| 2009/0214651 A1 | 8/2009 | Fugmann et al. |
| 2009/0216168 A1* | 8/2009 | Eckstein ......................... 602/43 |
| 2011/0028918 A1* | 2/2011 | Hartwell ............. A61M 1/0088 604/319 |

FOREIGN PATENT DOCUMENTS

| DE | 10 2005 027656 A1 | 12/2006 |
| DE | 10 2006 016636 A1 | 10/2007 |
| EP | 0426422 A2 | 5/1991 |
| EP | 0 630 629 B1 | 11/1994 |
| EP | 0486522 B1 | 12/1994 |
| EP | 0457977 B1 | 2/1995 |
| EP | 0691113 * | 5/1995 ............. A61F 13/00 |
| EP | 0 455 324 B1 | 6/1995 |
| EP | 0665856 B1 | 8/1995 |
| EP | 0 567 704 B1 | 2/1997 |
| EP | 0 528 091 B1 | 4/1997 |
| EP | 0 693 913 B1 | 3/1998 |
| EP | 0541391 B1 | 6/1998 |
| EP | 0541390 B1 | 7/1998 |

(Continued)

OTHER PUBLICATIONS

Contact Angle: retrieved from internet: http://en.wikipedia.org/wiki/Contact_angle. Retrieved on Apr. 16, 2013.

*Primary Examiner* — Robert A Wax
*Assistant Examiner* — Danah Al-Awadi
(74) *Attorney, Agent, or Firm* — Dilworth & Barrese, LLP (57) ABSTRACT

The present invention relates to a multilayered wound dressing particularly for wound treatment in the granulation and epithelization phase. The wound dressing comprises a) a first layer as a wound contact layer having a first side and a second side, and b) at least one second layer as an absorbent layer having a first side and a second side and comprising a hydrophilic polyurethane foam, wherein the polyurethane foam comprises a water fraction of at least 10% by weight of water.

27 Claims, 2 Drawing Sheets

(56) References Cited

FOREIGN PATENT DOCUMENTS

| | | | |
|---|---|---|---|
| EP | 0691113 | 7/2000 | |
| EP | 0691113 B1 | 7/2000 | |
| EP | 0 570 430 B1 | 1/2002 | |
| EP | 0855921 B1 | 1/2002 | |
| EP | 1007597 B1 | 4/2003 | |
| EP | 1082146 B1 | 4/2005 | |
| EP | 1156838 B1 | 5/2005 | |
| EP | 1658865 B1 | 1/2010 | |
| GB | 2428581 | 2/2007 | |
| WO | 9213576 A1 | 8/1992 | |
| WO | 9423678 A1 | 10/1994 | |
| WO | WO 02/45761 * | 12/2001 | ............ A61K 15/22 |
| WO | 0236097 A1 | 5/2002 | |
| WO | 2002/45761 A1 | 6/2002 | |
| WO | 0247761 A2 | 6/2002 | |
| WO | 03011352 A1 | 2/2003 | |
| WO | 03086255 A1 | 10/2003 | |
| WO | 2003/092756 A1 | 11/2003 | |
| WO | 2004052415 A1 | 6/2004 | |
| WO | WO 2007/113453 * | 4/2006 | ............ A61L 15/42 |
| WO | 2008/055586 A1 | 5/2008 | |

* cited by examiner

WOUND DRESSING

BACKGROUND OF THE INVENTION

This invention concerns wound dressings particularly as wound treatment means in the granulation and epithelization phase. These wound dressings are useful for moist treatment of wounds in particular. The present invention further concerns a process for producing these wound dressings.

The healing of skin wounds is based on the ability of the skin to regenerate epithelium and also connective and supporting tissue. Regeneration itself is characterized by a complex interplay of overlapping cellular activities which advance the healing process step by step. Three essential healing phases of a wound have been described in the literature irrespective of the type of wound. They include the inflammatory or exudative phase for blood coagulation and wound cleaning (phase 1, cleaning phase), the proliferative phase for building granulation tissue (phase 2, granulation phase) and the differentiation phase for epithelization and scar formation (phase 3, epithelization phase).

Numerous proposals for augmenting individual wound healing phases are described in the literature. Especially wound dressings comprising polyurethane foams have for some time been the subject matter of numerous articles in the technical literature and also of patent documents. The European patents EP 457 977 B1, EP 486 522 B1, EP 541 390 B1, EP 541 391 B1, EP 570 430 B1, EP 665 856 B1, EP 691 113 B1, EP 693 913 B1 or EP 1 082 146 B1, for instance, describe wound dressings having various constructions where the absorbent layer comprises a polyurethane foam. These polyurethane foams can become adherent to the healing wound when new cells/tissues grow into the pores of the foams.

In addition, the European patents EP 855 921 B1 and EP 1 156 838 B1 disclose wound dressings comprising a polyurethane foam coated with a hydrophobic silicone gel. This silicone gel is said to inhibit the adherence of the wound to the polyurethane foam.

Furthermore, the international applications WO 02/38 097 A1, WO 02/47 761 A1, WO 03/011 352 A1, WO 03/086 255 A1, WO 2004/052 415 A1 or EP 1 658 865 A1 describe wound dressings comprising a hydrogel and a polyurethane foam. The polyurethane foams used are dry.

Proceeding from these described and commercially available wound dressings, the present invention has for its object to provide an improved wound dressing particularly for wound healing in the granulation and/or epithelization phase. It is a further object of the present invention to provide a wound dressing that influences the pathological state of a wound such that a normal, natural wound healing process can occur. To this end, the wound dressing shall provide a sufficient amount of moisture to the wound and at the same time have a good absorptive capacity. It is yet a further object of the present invention to provide a wound dressing that exerts little if any shearing forces on a wound to be treated.

SUMMARY OF THE INVENTION

I have found that these objects are achieved by a multilayered wound dressing according to claim 1. Accordingly, a multilayered wound dressing which is in accordance with the present invention comprises a first layer as a wound contact layer having a first side and a second side, and at least one second layer as an absorbent layer having a first side and a second side and comprising a hydrophilic polyurethane foam, wherein the polyurethane foam comprises a water fraction of at least 10% by weight of water.

More particularly, the second layer of a wound dressing which is in accordance with the present invention comprises a hydrophilic polyurethane foam comprising a water fraction of at least 20% by weight of water, more particularly at least 30% by weight and most preferably at least 35% by weight of water. It is further preferable for the polyurethane foam to comprise a water fraction of at most 80% by weight of water, more particularly at most 70% by weight and most preferably at most 65% by weight of water. More particularly, this water fraction is homogeneously distributed in the polyurethane matrix of the foam. More particularly, the hydrophilic polyurethane foam comprises a water fraction of at least 10% by weight and at most 80% by weight of water and the distribution of water in the polyurethane foam is homogeneous in particular.

Here and hereinbelow, every content of an ingredient is to be understood in connection with the present invention—unless otherwise stated—as being in percent (%) by weight based on the weight of the component comprising the ingredient.

The amount of water in the respective component is defined in connection with the present invention on the basis of the DIN EN 14079 standard, wherein the amount of water is computed as follows:

$$W_w = \frac{W_g - W_t}{W_g} \cdot 100\% \tag{1}$$

where $W_w$=weight of water in % based on total weight of component
$W_g$=weight of water-containing component
$W_t$=weight of dry component Hence in connection with the present invention a polyurethane foam having a water fraction of at least 10% by weight is to be understood as being a polyurethane foam that comprises at least 10% by weight of water that can be released by the polyurethane foam. In contradiction thereto, what is not meant is the fraction of water possibly used for forming for example in the polymerization of the starting materials of the polyurethane foam. This water is covalently bonded and is not available for wound treatment. Nor is meant any water fraction used in the course of the production of the foam. This water fraction is withdrawn from the polyurethane foam, after or during its formation, usually by drying, for example by drying in an oven, and thus is also not available for wound treatment. Hence a wound dressing which is in accordance with the present invention includes a polyurethane foam that comprises a water fraction which distinctly exceeds any residual water content due to the production process, after drying.

A wound dressing which is in accordance with the present invention further preferably comprises a hydrophilic polyurethane foam having a retention value R of at least 20%. Further preferably, the hydrophilic polyurethane foam has a retention value R of at least 30%, more particularly of at least 40%, more particularly of at least 40% and most preferably of at least 50%.

Independently, it may further be preferable for the wound dressing to include a hydrophilic polyurethane foam having a retention value R of at most 90%, more particularly of at most 80% and very particularly of at most 70%. This retention value R is determined as per a method described herein.

It is very particularly preferable for a wound dressing which is in accordance with the present invention to comprise a hydrophilic polyurethane foam comprising a water fraction of at least 10% by weight wherein the water fraction corresponds to the retention value R of the polyurethane foam.

It is thus possible to provide a polyurethane foam wound dressing that is optimally conditioned for state of the art wound treatment, since, owing to the water content in the polyurethane foam, a wound surface to be treated is provided by the wound dressing with a particularly wound healing promoting climate immediately after application. The wound is supplied with moisture or water from the start, while the wound dressing simultaneously possesses a sufficient absorptive capacity due to the absorbing polyurethane foam. This removes from the wound surface any negative factors for wound healing, and at the same time provides moisture and water in a sufficient amount. Owing to the somewhat lower absorptive capacity compared with dry polyurethane foams, which do not comprise releasable water and usually absorb a lot of wound exudate very quickly, resulting in a dry wound surface, this wound dressing is very suitable for use in the epithelization or granulation phase of wound healing. So the wound dressing of the present invention is able to promote the granulation and/or epithelization of the wound to a particular degree in a natural manner.

In addition, a wound dressing which compared with wound dressings comprising dry hydrophilic polyurethane foams exerts a very much smaller shearing stress on the wound can be provided. A water fraction of at least 10% by weight of water in the polymer foam makes it possible to provide a wound dressing having a preconditioned hydrophilic polyurethane foam and a very much smaller swell capacity in relation to absorption of liquids compared with a wound dressing having a dry hydrophilic polyurethane foam. The lower swell capacity of the preconditioned polyurethane foam thus ensures that, within the wound dressing, lower shearing forces prevail in respect of further plies or materials as well as in respect of a wound to be treated. This makes it possible to provide a polyurethane foam wound dressing that is particularly promotive in respect of wound healing.

Hence, in accordance with a further developed concept, the present invention also provides a wound dressing comprising a second ply having a first side and a second side, wherein the ply comprises a hydrophilic polyurethane foam comprising a water fraction of at least 10% by weight and having a swell capacity $\Delta V_1$ of at most 80%. More particularly, this hydrophilic polyurethane foam has a swell capacity $\Delta V_1$ of at most 60%, more particularly of at most 40%, more particularly of at most 30% and most preferably of at most 20%. It may further be advantageous in this connection for the polyurethane foam to have a residual swell capacity $\Delta V_1$ of at least 5%. This residual swell capacity can be utilized to achieve better contact between the wound dressing and the floor of the wound during absorption.

Swell capacity $\Delta V_1$ of a polyurethane foam is to be understood as meaning the increased volume a polyurethane foam which has completely exhausted its absorptive capacity has compared with a polymer foam having a water content of at least 10% by weight of water. This swell capacity shall be determined as per a test described herein.

The polyurethane foam useful in connection with the present invention can be any hydrophilic polyurethane foam customary in state of the art wound treatment and absorbing a water fraction in its polyurethane matrix and having sufficient absorbency. Hence, in connection with the present invention, a hydrophilic polyurethane foam is a hydrophilic polyurethane foam that is capable of imbibing and storing, i.e., absorbing, a liquid in its polyurethane matrix and in its pores, and of rereleasing at least some of the imbibed liquid. Useful hydrophilic polymer foams include more particularly open-celled hydrophilic polyurethane foams. Accordingly, a particularly preferred wound dressing comprises a second layer comprising an open-celled hydrophilic polyurethane foam.

The present invention requires the use of such polyurethane foams as have a high absorptive capacity. This absorptive capacity shall be present even though the polyurethane foam has imbibed in its polymer matrix a fraction of its own weight of water. In a further development of the invention, therefore, a wound dressing that is in accordance with the present invention comprises a polyurethane foam comprising a water fraction of at least 10% by weight and at most 80% by weight of water and having a free absorbency $A_2$ of at least 10 g/g, more particularly at least 12 g/g and most preferably of at least 15 g/g, the free absorbency $A_2$ being determined as per DIN-EN 13726-1 (2002). The free absorbency $A_2$ here is the free absorbency of the water-containing polyurethane foam.

It is further preferable for a wound dressing that is in accordance with the present invention to comprise a polyurethane foam comprising a water fraction of at least 10% by weight and at most 80% by weight of water and having a free absorbency $A_1$ of at least 10 g/g, more particularly at least 12 g/g and most preferably of at least 15 g/g, the free absorbency $A_1$ being determined as per DIN-EN 13726-1 (2002). The free absorbency $A_1$ here is the free absorbency of the dry polyurethane foam.

It is further preferable for a wound dressing that is in accordance with the present invention to comprise a hydrophilic polyurethane foam that has an average pore size of less than 1000 µm, more particularly in the range from 100 to 1000 µm, more particularly in the range from 100 to 500 µm and most preferably in the range from 100 to 300 µm. More particularly, the average pore size on the first side of the second layer may be equal to the pore size in the interior of the second layer and/or the same size as on the second side of the second layer. Further preferred hydrophilic polyurethane foams have a density of less than 150 kg/m³, more particularly less than 140 kg/m³ and most preferably in the range from 50 to 120 kg/m³.

Particularly advantageous embodiments further comprise wound dressings comprising a polyurethane foam having a layer thickness in the range from 0.1 to 5.0 mm. More particularly, therefore, a wound dressing that is in accordance with the present invention includes an absorbent layer having a layer thickness in the range from 0.1 to 5.0 mm, more particularly in the range from 0.5 to 5.0 mm and most preferably in the range from 0.5 to 3.0 mm. Wound dressings having such layer thicknesses are able to imbibe a wound's exudate and at the same time can provide a sufficient amount of water or moisture to a wound. These layer thicknesses can be the same at every point of the wound contact layer, or differ in various regions of the wound contact layer. In one particular embodiment, the absorbent layer or the polyurethane foam also has flattened edges.

The wound contact layer according to the present invention may utilize any material that has no adverse effect on wound healing. It is the wound contact layer which is in direct contact with the wound when the wound dressing of the present invention is used. This wound contact layer can have the sole purpose of spacing the polyurethane foam away from the wound to be treated, but this wound contact layer can also perform further functions in relation to the wound dressing as well as in relation to the wound to be treated. More particularly, a wound dressing that is in accordance with the present invention may comprise a wound contact layer having a first side and a second side, in which case the wound contact layer comprises a hydrogel matrix, a polymer film, a hydrocolloid matrix, a polymer net, a nonwoven or an adhesive.

In a further development of the wound dressing of the present invention, the wound contact layer may comprise a multiplicity of channels, openings or holes to let liquids pass through the wound contact layer. A more particular provision in this connection is for the wound contact layer to include channels which form a passageway for wound exudates from the first side to the second side. In this embodiment, the first side of the wound contact layer is in direct contact with a wound to be treated and the second side of the wound contact layer is in direct contact with the first side of the absorbent layer.

In a further development of the present invention the wound contact layer may also have channels, openings or holes from 0.5 to 5 mm in diameter. More particularly, the wound contact layer includes channels, openings or holes from 1 to 3 mm in diameter. It is very particularly preferable for the wound contact layer to have on its first side (the side which faces the wound when the wound dressing is used as intended) openings from 1 to 3 mm in diameter, while the second side of the wound contact layer is in direct contact with the polyurethane foam.

It may further be preferable for the wound contact layer to have a multiplicity of channels, openings or holes to allow liquids to pass through the wound contact layer, which channels, openings or holes on the first side of the wound contact layer occupy an area of at most 95% of the area of the first side of the wound contact layer. It is further preferable in this connection for the channels, openings or holes to occupy an area of at most 70%, more particularly at most 50%, more particularly at most 40% and most preferably of at most 30% of the area of the first side of the wound contact layer. It is very particularly preferable for the wound contact layer to have channels, openings or holes which on the first side of the layer occupy an area of at least 5% and at most 30% of the area of the first side of the wound contact layer. In a very particular embodiment, the wound dressing includes a wound contact layer having from 2 to 8 holes per $cm^2$. One possibility here is for the wound contact layer to be a perforate polymer film or a polymer net, more particularly a polyurethane film or a polymer net.

In a further embodiment of the present invention, it may further be possible for a wound dressing that is in accordance with the present invention to comprise a hydrocolloid matrix as wound contact layer. This hydrocolloid matrix can consist of a tacky polymer matrix into which hydrocolloid particles have been dispersed. For the purposes of the present invention, a hydrocolloid is a material which is a hydrophilic synthetic or natural polymer material which is soluble or absorbent and/or swelling in water. Preferably, a wound contact layer comprises a hydrocolloid composed of a synthetic or natural polymer material selected from the group consisting of alginic acid and salts thereof and also derivatives thereof, chitin or its derivatives, chitosan or its derivatives, pectin, cellulose or its derivatives such as cellulose ethers or cellulose esters, crosslinked or uncrosslinked carboxyalkylcellulose or hydroxyalkyl-cellulose, polyvinyl alcohol, polyvinylpyrrolidone, agar, guar gum, gelatin and mixtures thereof.

The hydrocolloid can be present not only in the form of fibers but also in the form of particles and/or fibers within a matrix. More particularly, the hydrocolloid can be present in the form of particles in a tacky polymer matrix. The tacky polymer matrix comprises at least one block copolymer selected from the group consisting of AB diblock copolymers and/or ABA triblock copolymers, which is constructed from the monomers styrene, butadiene and isoprene. The proportion of hydrocolloid particles in the wound contact layer may preferably include 10% to 70% by weight based on the total weight of the wound contact layer. Such a composition is disclosed in EP 1 007 597 B1 for example.

In a further embodiment of the present invention, a wound dressing that is in accordance with the present invention may further comprise a water-containing hydrogel matrix as wound contact layer. This hydrogel matrix may preferably comprise at least 20% by weight, more particularly at least 30% by weight, more particularly at least 40% by weight and most preferably at least 50% by weight of water, in which case the hydrogel matrix further preferably comprises at most 90% by weight and further preferably at most 80% by weight of water. It is thus possible to provide a wound dressing which includes a wound contact layer which, in addition to the water-containing polyurethane foam, contains a second water-containing component and thus provides moisture in an amount sufficient for natural wound healing.

Useful water-containing hydrogel matrices in connection with the present invention include in particular hydrogel matrices that form a coherent, discrete layer and do not release water under pressure. More particularly, useful hydrogel matrices in connection with the present invention comprise a polyurethane-polyurea copolymer. This polyurethane-polyurea copolymer may be formed more particularly from a prepolymer having aliphatic diisocyanate groups and a polyamine based on polyethylene oxide. More particularly, the polyurethane-polyurea copolymer may be formed from a prepolymer having isophorone diisocyanate ends, a polyamine based on polyethylene oxide, and water. These hydrogel matrices are particularly useful for storing water and delivering this water to a wound.

It is further preferable for the water-containing hydrogel matrix to further comprise at least one polyhydric alcohol from the group of dihydric, trihydric, tetrahydric, pentahydric or hexahydric alcohols. More particularly, the alcohol can be selected from the group of glycols, more particularly ethylene glycol or propylene glycol, and sorbitol or glycerol or mixtures thereof. These alcohols are outstandingly useful as moisture donors and thus constitute a care component for the skin surrounding the wound.

In this connection, the water-containing hydrogel matrix may comprise in particular from 0% to 50% by weight of a polyhydric alcohol. More particularly, the hydrogel matrix comprises from 5% to 40% by weight of a polyhydric alcohol and most preferably from 10% to 30% by weight of a polyhydric alcohol.

In addition, the water-containing hydrogel matrix may comprise in particular at least one salt. More particularly, in this connection, the hydrogel matrix comprises an inorganic salt. Of particular suitability in this connection are chlorides, iodides, sulfates, hydrogensulfates, carbonates, bicarbonates, phosphates, dihydrogenphosphates or hydrogenphosphates of alkali and alkaline earth metals. It is very particularly preferable for the hydrogel matrix to comprise sodium chloride, potassium chloride, magnesium chloride, calcium chloride or mixtures thereof. These salts are particularly good in simulating the electrolyte mixture in a wound serum.

As a result, a hydrogel matrix comprising these salts provides a wound with a climate that is particularly promotive of wound healing.

One possibility here is for the hydrogel matrix to comprise from 0% to 5% by weight of at least one salt. More particularly, the hydrogel matrix comprises from 0.1% to 3% by weight of a salt and most preferably from 0.5% to 1.5% by weight of a salt.

All together, in a possible embodiment of the present invention, the water-containing hydrogel matrix preferably comprises at least 20% by weight of water and at least 10% by weight of polyurethane-polyurea copolymer. A further preferred hydrogel matrix comprises at least 20% by weight of water and at least 15% by weight of polyurethane-polyurea copolymer. In a further preferred embodiment, the hydrogel matrix is formed from 6% to 60% by weight of a prepolymer having aliphatic diisocyanate groups, 4% to 40% by weight of polya mine based on polyethylene oxide, 0% to 50% by weight of a polyhydric alcohol, 0% to 5% by weight of at least one salt selected from the group consisting of sodium chloride, potassium chloride, magnesium chloride, calcium chloride and mixtures thereof, and at least 20% by weight of water.

In a further preferred embodiment, the hydrogel matrix is formed from 6% to 30% by weight of a prepolymer having aliphatic diisocyanate groups, 4% to 20% by weight of diamine based on polyethylene oxide, 10% to 30% by weight of a polyhydric alcohol selected from the group consisting of propylene glycol and/or glycerol, 0.5-1.5% by weight of a salt selected from the group consisting of sodium chloride, potassium chloride, magnesium chloride, calcium chloride or mixtures thereof, and at least 30% by weight of water.

In a very particularly preferred embodiment, the hydrogel matrix is formed from 6% to 20% by weight of prepolymer having isophorone diisocyanate ends, 4% to 15% by weight of diamine based on polyethylene oxide, 15% to 20% by weight of polypropylene glycol and/or glycerol, 0.5% to 1.5% by weight of a salt selected from the group consisting of sodium chloride, potassium chloride, magnesium chloride, calcium chloride or mixtures thereof, and at least 40% by weight of water. This hydrogel matrix has a free absorbency $A_3$ (measured to DIN EN 13723-1 (2002)) of at least 1 g/g and at most 5 g/g, constitutes a nonirritant, liquid-absorbing, cushioning, skinlike medium that affords protection against bacteria, and thus is particularly suitable for use as a wound contact layer.

Particularly advantageous embodiments further comprise wound dressings comprising a hydrogel matrix having a layer thickness in the range from 0.1 to 5.0 mm. More particularly, therefore, a wound dressing that is in accordance with the present invention includes a wound contact layer having a layer thickness in the range from 0.1 to 5.0 mm, more particularly in the range from 0.5 to 5.0 mm and most preferably in the range from 0.5 to 3.0 mm. Wound dressings having such layer thicknesses do not stick wounds on the one hand and on the other hand are able to imbibe a wound's exudate and convey it onto the absorbent layer. These layer thicknesses can be the same at every point of the wound contact layer, or differ in various regions of the wound contact layer.

It is further preferable for the hydrogel matrix to comprise channels, more particularly conical channels, to allow liquids to pass through from the first to the second side. This provides for improved passage of wound exudate in particular. It is particularly preferable for the channels to have an elliptical or circular cross section, i.e., for the channels to have a circular or elliptical opening both on the first side and on the second side of the hydrogel matrix and for the circular or elliptical opening on the first and second sides to differ in size. However, the channels may also have a triangular, rectangular, square, pentagonal, hexagonal or some other polygonal cross section. It is very particularly preferable for the first side to have openings larger than the opening on the second side.

In a further development of the invention, the wound contact layer or the hydrogel matrix may also have openings from 0.5 to 5 mm in diameter. More particularly, the wound contact layer or the hydrogel matrix will have openings from 1 to 3 mm in diameter. It is very particularly preferable for the wound contact layer or the hydrogel matrix to have openings on the wound-facing first side which are from 1 to 3 mm in diameter, while the second side of the wound contact layer or of the hydrogel matrix is in direct contact with the polyurethane foam. A transition layer may also be disposed between the absorbent layer and the wound contact layer. In this embodiment, a wound dressing that is in accordance with the present invention includes, between the hydrogel matrix and the polyurethane foam, a layer which comprises both the materials. This transition layer may have channels, openings or holes, just like the wound contact layer. When the transition layer has channels, openings or holes, it is a further preferred embodiment that these channels, openings or holes are filled with polyurethane foam. It is further preferable for these channels, openings or holes to be congruent to the channels, openings or holes in the wound contact layer. Providing such a transition layer makes it possible to provide a wound dressing comprising a laminate formed from a polyurethane foam and a hydrogel matrix and having a particularly firm bond between the absorbent layer and the wound contact layer.

In accordance with another further developed concept of the present invention, the present invention also provides a wound dressing which includes a barrier layer between the hydrogel matrix and the hydrophilic polymer foam. Such a barrier layer may comprise for example a polymer film with openings.

A wound dressing that is in accordance with the present invention may further comprise a backing layer. This backing layer can consist of various materials. Typically, wound dressings utilize textile backing materials, nonwovens, polymer films or polymer foams. This backing layer may be in direct or indirect contact with the second side of the absorbent layer or with the hydrophilic polymer foam. In the case of direct contact, the backing layer is laminated directly onto the absorbent ply or the polyurethane foam, whereas in the case of indirect contact the backing layer is applied to the absorbent layer or the polyurethane foam by means of an adhesive. This adhesive may be applied between the backing layer and the absorbent layer in a uniform manner or merely in sub-regions.

The backing layer of a wound dressing that is in accordance with the present invention may utilize in particular polymer films or polyurethane foams. Very particular preference is given to polymer films or polymer foams which are water impermeable and have a high moisture vapor permeability. Films or foams particularly suitable for this are fabricated from polyurethane, polyether urethane, polyester urethane, polyether-polyamide copolymers, polyacrylate or polymethacrylate. More particularly, a water impermeable and moisture vapor permeable polyurethane film or a water impermeable and moisture vapor permeable polyurethane foam is suitable for use as backing layer. More particularly, a polyurethane film, polyester urethane film or polyether urethane film is preferable for use as polymer film. However, very particular preference is also given to polymer films from 15 to 50 µm, more particularly from 20 to 40 µm and most preferably from 25 to 30 µm in thickness. The moisture vapor transmission rate of the polymer film of the wound dressing is preferably at least 750 g/m²/24 h, more particularly at least 1000 g/m²/24 h and most preferably at least 2000 g/m²/24 h (measured to DIN EN 13726). In particularly preferred embodiments, these films have a moisture-proof tacky edge portion. This edge portion ensures that the wound dressing can be applied to and fixed at its intended location. It is further ensured that liquid cannot escape between the film and the skin surrounding the area to be treated. Particularly preferable adhesives achieve in a thin add-on of 20 to 35 g/m² a moisture vapor transmission rate combined with the film of at least 800 g/m²/24 h and preferably of at least 1000 g/m²/24 h (measured to DIN EN 13726).

In accordance with a further developed concept of the present invention, the present invention likewise provides a multilayered wound dressing comprising a backing layer, an absorbent layer, a hydrophilic wound contact layer and a distributor layer, wherein the wound contact layer comprises a hydrophilic polyurethane elastomer. More particularly, the absorbent layer is bonded to the wound contact layer. Such a wound dressing very advantageously includes, between the backing layer and the absorbent layer, a distributor layer which consists of a hydrophilic polyurethane foam in particular. The distributor layer provides for distribution of the imbibed wound fluids over the entire area of the wound dressing particularly above the absorbent layer, i.e., the wound fluids are imbibed not just in the z-direction (away from the wound, in the direction of the backing layer), but also in the x-y-direction (over the area of the wound dressing).

In accordance with a further developed concept, the present invention also provides a process for producing a multilayered wound dressing. More particularly, the present invention provides a process for producing an above-described wound dressing. This process comprises the steps of
a) providing a polyurethane foam,
b) applying at least 10% by weight of water to the polyurethane foam, and
c) laminating the water-containing polyurethane foam produced under b) to a wound contact layer.

More particularly, the amount of water applied to the polymer foam in this process amounts to at least 10% by weight and at most 80% by weight and the water is applied by spraying or dipping.

It must be noted here that the herein recited features of the preferred or alternative embodifications of the inventions shall not be restricted to the individual preferences or alternatives. On the contrary, the combination of the embodifications or the combination of the individual features of the alternative forms must similarly count as belonging to an embodification according to the present invention. Similarly, the invention must not be understood as being reduced by the following description of the drawings, where

DESCRIPTION OF THE PREFERRED EMBODIMENT(S)

Figure 1:
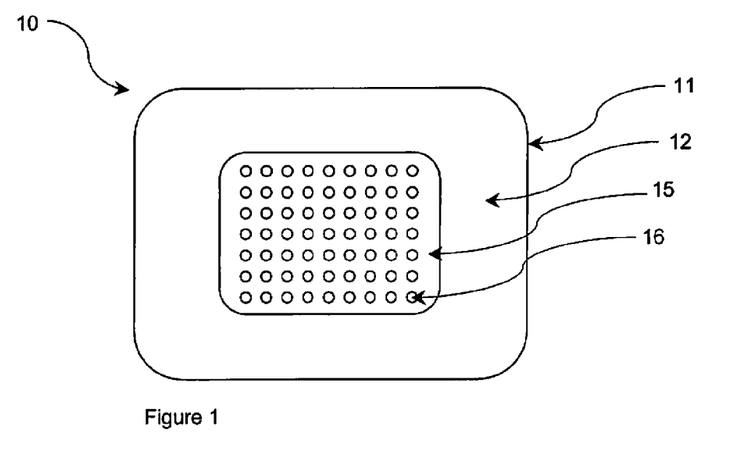
FIG. 1: shows a first inventive wound dressing.

FIG. 1 shows a first inventive wound dressing (10) with the wound contact layer in plan view. The wound dressing (10) is fabricated as a so-called island dressing and consists of a backing layer (11) composed of a water impermeable and moisture vapor permeable polyurethane film uniformly coated with an acrylate adhesive (12). In the center of the backing layer the acrylate adhesive (12) has been used to apply an absorbent hydrophilic polyurethane foam layer (not depicted here) onto which a polyurethane film (15) has been applied as wound contact layer. This hydrophilic polyurethane foam layer comprises a water fraction of 40% by weight of water. Therefore, 100 g of a polyurethane foam used in this example comprise 40 g of water and 60 g of polyurethane matrix. The polyurethane film (15) is adhesively bonded to the absorbent polyurethane foam (not depicted here). A multiplicity of circular holes (16) have been made in the polyurethane film to allow wound exudate to flow therethrough from the wound into the absorbent layer. The polyurethane film prevents ingrowth of newly formed cells into the pores of the polyurethane foam.

Figure 2:
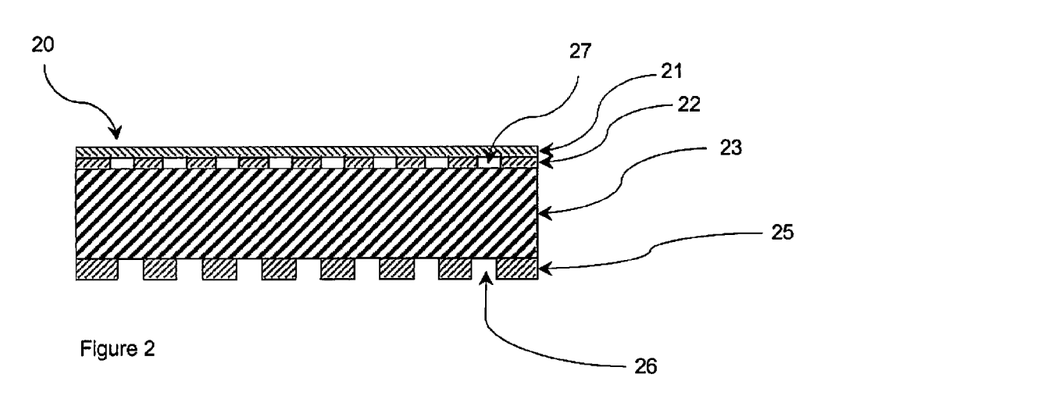
FIG. 2: shows a second inventive wound dressing in cross section.

FIG. 2 shows a further embodiment of an inventive wound dressing. The wound dressing (20) comprises a backing layer (21) which is congruent to an absorbent layer (23), is composed of a water impermeable and moisture vapor permeable polyurethane foam and is bonded by a discontinuous adhesive layer (22) of an acrylate adhesive to the absorbent layer (23). The discontinuous add on means that there are regions (27) of the absorbent layer and of the backing layer which remain unconnected. The wound dressing comprises an absorbent layer (23) having a layer thickness of 4 mm and a backing layer (11) having a layer thickness of 1.5 mm. The absorbent layer (23) is formed from an open-celled hydrophilic polyurethane foam having an average pore size of 220 µm. The polyurethane foam in question comprises a water fraction of 70% by weight. On the first side of the polyurethane foam is a polyurethane adhesive applied as a wound contact layer (25). The form in which the polyurethane adhesive has been applied to the polyurethane foam at a basis weight of 75 g/m² is not continuous, so that the wound contact layer (25) has circular holes (26) for improved passage of wound exudate. The polyurethane foam comprises a first side having an area of 25 cm², of which the holes (26) altogether occupy an area of 5 cm².

Figure 3:
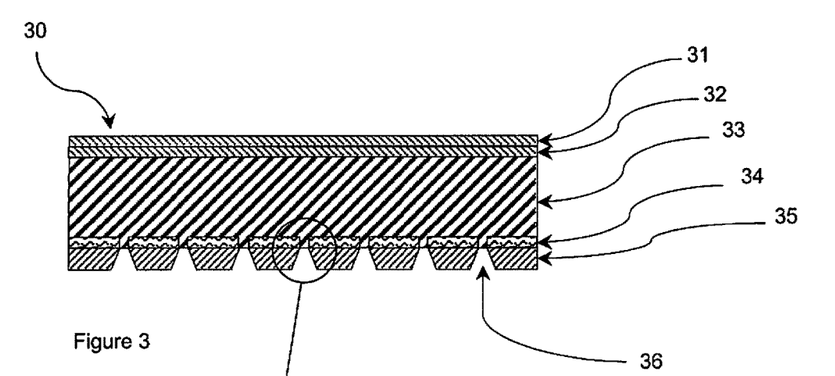
FIG. 3 shows a third inventive wound dressing in cross section.
Figure 3A:
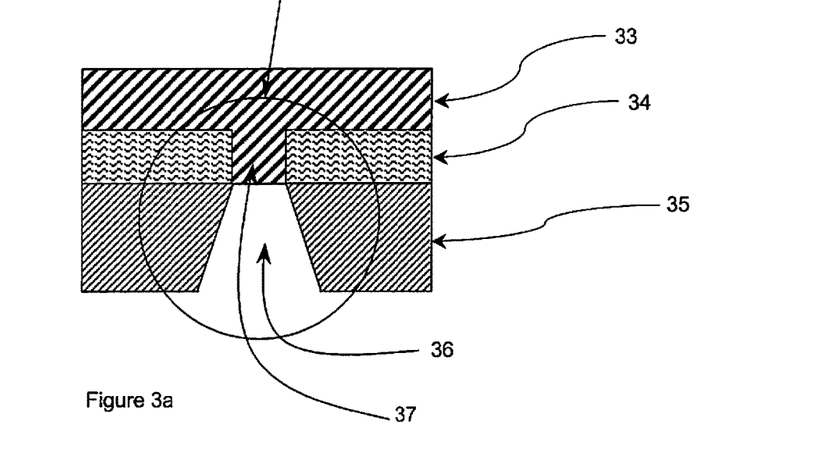
FIG. 3a shows a detail from the third inventive wound dressing in cross section.

FIG. 3 shows a third embodiment of an inventive wound dressing. The wound dressing (30) comprises a backing layer (31) composed of a water impermeable and moisture vapor permeable polyurethane film, an absorbent layer (33) composed of an open-celled hydrophilic polyurethane foam having a water fraction of 52.8% by weight (based on the polyurethane foam) and a wound contact layer (35) composed of a water-containing hydrogel matrix having a water fraction of about 63.5% by weight (based on the hydrogel). The backing layer (31) is uniformly laminated onto the hydrophilic polymer foam by means of an acrylate adhesive (32) applied to the polymer film. A water-containing hydrogel matrix (35) comprising a polyurethane-polyurea copolymer has been applied to the absorbent layers first side, which faces the wound in use. The hydrogel matrix is endowed with conical channels (36) which are circular in cross section (parallel to the wound), and so an improved wound exudate flow from the wound into the absorbent hydrophilic foam can take place (cf. FIG. 3a). In the course of the production of the wound dressing, the still viscous hydrogel matrix has slightly penetrated into the polyurethane foam, forming between the hydrogel matrix and the hydrophilic polyurethane foam a transition layer (34) which consists of the hydrogel matrix and the hydrophilic polyurethane foam. The transition layer in turn has channels (37)

which are filled with polyurethane foam only and which are disposed congruent relative to the channels in the hydrogel matrix.

EXAMPLE

The wound dressing has the construction described using FIG. 3.

A) Producing the Hydrogel

The hydrogel is produced using the following aqueous solutions and components (components A, B, C):

Component A

| Propylene glycol USP30 (99.8%) | Hedinger Aug. GmbH; Stuttgart, Germany | 23.24% by weight |
|---|---|---|
| Aqua purificata | Water treatment plant | 75.41% by weight |
| NaCl, purest, USP | Hedinger Aug. GmbH; Stuttgart, Germany | 1.35% by weight |

Component A is produced by combining the ingredients and stirring until the salt has completely dissolved. Component A is cooled down to 2° C.

Component B

| Jeffamin ED-2003 | Huntsman; Everberg, Belgium | 52.5% by weight |
|---|---|---|
| Aqua purificata | Water treatment plant | 47.5% by weight |

The aqueous component B is produced by melting the solid Jeffamin at 50° C. and adding the melt to the initially charged water with stirring. Component B is cooled down to room temperature.

Component C

| Aquapol PI-13000-3 | Carpenter; Richmond, USA | 100.0% by weight |
|---|---|---|

Component C is brought to room temperature.

The ready-made components A, B and C are combined with each other in a ratio of 75.4:14.0:10.6 and homogenized by means of a rotating mixing system to form a homogeneous mixture which is poured ideally without bubbles into the molds provided.

B1) Polyurethane Foam Used

A hydrophilic polyurethane foam is used (polyurethane foam MCF.03R; from Corpura,—Etten Leur, Netherlands). The dry hydrophilic polyurethane foam has the following characteristics:

a) density: 77.9-83.7 kg/m$^3$ (EN ISO 845)
b) average pore size: Ø 208 µm (determined by microscope)
c) layer thickness: 2.7 mm (thickness measuring instrument with 25 cm$^2$ plate, 2 g/cm$^2$ load, measured to EN ISO 9073-2)
d) moisture vapor transmission rate: MVTR (upright)=3593 g/m$^2$/24 h (measured to DIN EN 13726-2)
e) absorbency: free absorbency $A_1$=20.5 g/g (measured to DIN EN 13726-1)
f) swell capacity: $\Delta V_0$=89.7%
   The swell capacity $\Delta V_0$ of a polyurethane foam describes the volume change experienced by a dry polyurethane foam after it has reached its maximum absorption. To determine swell capacity $\Delta V_0$ the spatial dimensions of a sample piece of the dry polymer foam and the spatial dimensions of this sample piece after complete absorption as per the free absorbency of DIN EN 13726-1 are determined. The thickness (height) is determined using a thickness measuring instrument having a 25 cm$^2$ plate adjusted to a loading of 2 g/cm$^2$ as per EN ISO 9073-2.

The lateral extent (length, width) is determined by means of a vernier without deforming the sample piece. To determine the extent, the particular sample piece is laid tensionlessly onto a smooth surface. The volume change after absorption corresponds to the swell capacity $\Delta V_0$ of the dry polyurethane foam, taking account of all three spatial directions.

| | Sample 1 | Sample 2 | Sample 3 | Mean | Change/mm (%) |
|---|---|---|---|---|---|
| Length ($l_0$)/mm | 50.0 | 50.0 | 50.0 | 50.0 | — |
| Width ($b_0$)/mm | 50.0 | 50.0 | 50.0 | 50.0 | — |
| Height ($h_0$)/mm | 2.80 | 2.81 | 2.81 | 2.81 | — |
| Length ($l_2$)/mm | 60.2 | 61.9 | 61.3 | 61.1 | 11.1 mm (22.2%) |
| Width ($b_2$)/mm | 61.7 | 63.5 | 62.8 | 62.7 | 12.7 mm (25.4%) |
| Height ($h_2$)/mm | 3.47 | 3.47 | 3.49 | 3.48 | 0.67 mm (23.8%) |

$$\Delta V_0 = \frac{V_2 - V_0}{V_0} \cdot 100\% = \frac{(l_2 \cdot b_2 \cdot h_2) - (l_0 \cdot b_0 \cdot h_0)}{(l_0 \cdot b_0 \cdot h_0)} \cdot 100\% = 89.7\%$$

where: $V_0$=the volume of the sample piece before absorption (measured under standard conditions (23° C., 50% relative humidity), and $V_2$=the volume of the sample piece after complete absorption.

g) Retention value: R=52.8%

The retention value R describes the amount of water which the polyurethane foam can maximally bind in its polyurethane matrix disregarding the water which might be imbibed into the pores. The retention value is determined by die cutting a sample piece of 5 cm×5 cm (stored under standard conditions) out of a hydrophilic polyurethane foam not more than 5 mm in thickness, the weight of which is measured under standard conditions. The sample piece is thereafter subjected to a free absorbency test with water similar to DIN EN 13726-1. The water imbibed by the pores is squeezed out of the sample piece by means of a roller (weight 5000 g, diameter 10 cm, width 5 cm) by the sample being repeatedly placed between fresh paper tissues and rollered. This operation is repeated until there is no visible water absorption in the paper tissues. To determine the retention value R, the water fraction $W_{ww}$, which is present in the polyurethane foam following the absorbing and squeezing out, is measured as per DIN EN 14079 and computed as follows:

| | Sample 1 | Sample 2 | Mean |
|---|---|---|---|
| Weight dry ($W_{tt}$) | 0.57 g | 0.58 g | 0.58 g |
| Weight after absorption | 11.44 g | 11.75 g | 11.60 g |
| Weight after squeezing out ($W_{gg}$) | 1.22 g | 1.24 g | 1.23 g |

The thickness of the sample pieces measured is 2.80 mm.

$$R = W_{ww} = \frac{W_{gg} - W_{tt}}{W_{gg}} \cdot 100\% = 52.8\%$$

(measured to DIN EN 14079)

where: $W_{ww}$=weight of water present in the polyurethane foam after absorption and squeezing out $W_{tt}$=weight of sample piece after drying, and $W_{gg}$=weight of sample piece after absorption and squeezing out B2) Conditioning the Polyurethane Foam The dry hydrophilic polyurethane foam is cut to a size of 20×30 cm and dipped in water for 3 minutes, so that the polyurethane foam reaches its maximum absorption. The polyurethane foam is removed from the water and carefully squeezed out by hand. The polyurethane foam is thereafter repeatedly placed between dry paper tissues and squeezed out by means of a roll (linear pressure 10 N/cm) until no water absorption is visible in the paper tissues. Therefore, the possibility of no water being present in the pores of the foam can be ruled out.

The water-containing polyurethane foam has the following characteristics:

a) Water content: The hydrophilic polyurethane foam has a water fraction $W_w$=52.8% by weight (measured to DIN EN 14079), which corresponds to the retention value R of the dry polyurethane foam.
b) Absorbency: Free absorbency $A_2$=16.2 g/g (measured to DIN EN 13726-1)
c) Swell capacity: $\Delta V_1$=4%

The swell capacity of the water-containing polyurethane foam is determined similarly to the dry polymer foam.

|  | Sample 1 | Sample 2 | Sample 3 | Mean | Change/mm (%) |
|---|---|---|---|---|---|
| Length ($l_1$)/mm | 62.8 | 64.3 | 64.15 | 63.75 | — |
| Width ($b_1$)/mm | 63.4 | 64.45 | 64.3 | 64.05 | — |
| Height ($h_1$)/mm | 3.4 | 3.38 | 3.39 | 3.39 | — |
| Length ($l_2$)/mm | 60.2 | 61.9 | 61.3 | 61.1 | 2.65 mm (4.3%) |
| Width ($b_2$)/mm | 61.7 | 63.5 | 62.8 | 62.7 | 1.35 mm (2.2%) |
| Height ($h_2$)/mm | 3.47 | 3.47 | 3.49 | 3.48 | −0.09 mm (−2.5%) |

$$\Delta V_1 = \frac{V_2 - V_1}{V_1} \cdot 100\% = \frac{(l_2 \cdot b_2 \cdot h_2) - (l_1 \cdot b_1 \cdot h_1)}{(l_1 \cdot b_1 \cdot h_1)} \cdot 100\% = 4\%$$

where: $V_1$=volume of water-containing sample piece and $V_2$=volume of sample piece after complete absorption.

C) Further Materials Used

The backing layer used is a water impermeable polyurethane film 60 μm in thickness (from Exopack-Wrexham, United Kingdom). This film is coated with an acrylate-based pressure sensitive adhesive in a layer 30 μm in thickness. The film has a moisture vapor transmission rate MVTR (upright) of 1100 g/m²/24 h (DIN EN 13726-1).

D) Producing the Wound Dressings

The wound dressings (specimens) are fabricated by hand in accordance with the following sequence:

1. The polyurethane foam is preconditioned as per B) and provided.
2. To produce a hydrogel matrix having channels a PTFE mold having a pimpled texture is provided. The pimples of the pimpled texture are cone-shaped and have an average diameter of 1.38 mm (base 1.56 mm, tip 1.2 mm). The pimples are 1.35 mm high and are spaced 5 mm apart in a rectangular pattern.
3. The hydrogel is produced as per A) and provided, although the hydrogel has to be further processed without delay after the commixing and homogenizing. To this end, the hydrogel is poured ideally without bubbles into the provided molds to form the hydrogel matrix.
4. The gel is distributed with a PTFE blade such that the gel layer has the height of the pimples (1.35 mm). Excess gel is removed from the mold.
5. After about 3 minutes, the preconditioned polyurethane foam is laid onto the gel surface. A pressure of 200 N/m² is applied to the foam to press and hold it down.
6. After about 7 minutes more, the gel has become bonded to the foam, so that the laminate of water-containing polyurethane foam and water-containing hydrogel matrix can be removed from the mold. A transition layer consisting of water-containing hydrogel matrix and water-containing polyurethane foam has formed in a thickness of 0.3 mm.
7. The laminate is placed with the hydrogel side face down onto the prepared release film (the siliconized side faces the gel), so that the side facing the wound is protected.
8. The assembly is covered on the foam side with a self-adhesive polyurethane film (cf. D), and the polyurethane film is firmly pressed in place using a pressure of 200 N/m².
9. Wound dressings having an edge length of 10×10 cm are die cut out of the multi-ply material assembly.

The wound dressing thus produced has the construction described using FIG. 3, although FIG. 3 does not show a release liner. The wound dressing thus consists of a laminate composed of a flexible water-containing hydrogel matrix as wound contact layer, which contains 63.5% by weight of water (based on the hydrogel matrix), and an absorbent layer composed of an open-celled hydrophilic polyurethane foam having a water fraction of 52.8% by weight (based on the polyurethane foam).

The wound dressing further has the following characteristics:

a) Basis weight: 1550 g/m² (measured to DIN EN 29073-1)
b) Absorbency: free absorbency $A_1$=56 g/100 cm² (measured to DIN EN 13726-1)
c) Water content in total:

$$W_w = \frac{W_g - W_t}{W_g} \cdot 100\% = 58.8\%$$

d) Swell capacity: $\Delta V$=10% (measured as per method described above)

The present wound dressing thus has a high water fraction, a high absorbency and a low swell. The wound dressing is thus optimally suitable for use in wound healing phases 2 and 3 (granulation phase and epithelization phase).

What is claimed is:

1. A multilayered wound dressing comprising
   a) a first layer as a wound contact layer having a first side and a second side, and a multiplicity of channels, and including a hydrogel matrix which comprises a polyurethane-polyurea copolymer formed from a prepolymer having aliphatic diisocyanate groups and a polyamine based on polyethylene oxide, and wherein the hydrogel matrix contains from 20% to 80% of wound deliverable water;
   b) at least one second layer as an absorbent layer having a first side and a second side and comprising a hydrophilic polyurethane foam which has a water fraction of at least 10% by weight and at most 80% by weight of water, a free absorbency $A_2$ of at least 10 g/g determined by DIN-EN13726-1 and a swell capacity $\Delta V_1$ of at most 60%; and,
   c) a transition layer disposed between the first layer and the second layer and which transition layer consists of a portion of the hydrogel matrix of the first layer which has penetrated into a portion of the polyurethane foam of the second layer, said transition layer having channels which are filled with only polyurethane foam from the second side of the second layer and which channels are disposed congruent relative to the channels in the hydrogel matrix of the first layer.

2. The wound dressing of claim 1, wherein the wound contact layer further comprises one or more of a polymer film, a hydrocolloid matrix, a polymer net, a nonwoven material or an adhesive.

3. The wound dressing according to claim 1 wherein the prepolymer having aliphatic diisocyanate groups includes isophorone diisocyanate.

4. The wound dressing according to claim 1, wherein the hydrogel matrix has channels from a first side to an opposite second side to allow liquids to pass through the hydrogel matrix.

5. The wound dressing of claim 1, wherein the wound dressing further comprises a water impermeable and moisture vapor permeable polymer film or a water impermeable and moisture vapor permeable polymer foam as a backing layer.

6. The wound dressing of claim 5 wherein the backing layer is the water impermeable and moisture vapor permeable polymer foam.

7. A multilayered wound dressing comprising
a) a first layer as a wound contact layer having a first side and a second side, and a plurality of channels extending from the first side to the second side, and including a hydrogel matrix which comprises a polyurethane-polyurea copolymer formed from a prepolymer having aliphatic diisocyanate groups and a polyamine based on polyethylene oxide, and wherein the hydrogel matrix contains from 20% to 80% of wound deliverable water;
b) at least one second layer as an absorbent layer having a planar first side and a second side and comprising a hydrophilic polyurethane foam, the first side being in contact with the wound contact first layer and, which has a water fraction of at least 10% by weight and at most 80% by weight of water, a free absorbency $A_2$ of at least 10 g/g determined by DIN-EN13726-1 and a swell capacity $\Delta V_1$ of at most 60%;
c) a transition layer disposed between the first layer and the second layer and which transition layer consists of a portion of the hydrogel matrix of the first layer which has penetrated into a portion of the polyurethane foam of the second layer, said transition layer having channels which are filled with only polyurethane foam from the second side of the second layer and which channels are disposed congruent relative to the channels in the hydrogel matrix of the first layer; and,
d) a water impermeable and moisture vapor permeable polymer film or a water impermeable and moisture vapor permeable polymer foam as a backing layer bonded to the second side of the polyurethane foam by a discontinuous layer of adhesive.

8. The multilayered wound dressing of claim 7 wherein the wound contact first layer comprises a hydrogel matrix and the channels are conically shaped.

9. The multilayered wound dressing of claim 7 wherein the wound contact first layer further comprises a hydrocolloid matrix comprising a tacky polymer into which hydrocolloid particles have been dispersed.

10. The multilayered wound dressing of claim 9 wherein the hydrocolloid particles comprise one or more of alginic acid, salts of alginic acid. chitin, chitosan, pectin, cellulose, cellulose ethers, cellulose esters, crosslinked or uncrosslinked carboxyalkylcellulose or hydroxyalkylcellulose, polyvinyl alcohol, polyvinylpyrrolidone, agar, guar gum, gelatin, and combinations thereof.

11. The multilayered wound dressing of claim 9 wherein the tacky polymer matrix comprises at least one block copolymer selected from the group consisting of AB diblock copolymers and ABA triblock copolymers, wherein said block copolymers are constructed from the monomers selected from the group consisting of styrene, butadiene and isoprene.

12. The wound dressing of claim 1 wherein the hydrogel matrix includes 5-40 wt % of a polyhydric alcohol.

13. The wound dressing of claim 12 wherein the polyhydric alcohol is selected from the group consisting of ethylene glycol, polypropylene glycol, sorbitol, glycerol and combinations thereof.

14. The wound dressing of claim 1 wherein the hydrogel matrix includes 0.1-3.0 wt % of a salt.

15. The wound dressing of claim 14 wherein the salt is selected from the group consisting of sodium chloride, potassium chloride, magnesium chloride, calcium chloride and combinations thereof.

16. The wound dressing of claim 1 wherein the hydrogel matrix is formed from a 6-30 wt % of a prepolymer having aliphatic diisocyanate groups, 4-20 wt % of a diamine based on polyethylene oxide, 10-30 wt % polyhydric alcohol selected from ethylene glycol, polypropylene glycol, sorbitol, glycerol and combinations thereof, 10-30 wt % of a polyhydric alcohol selected from polypropylene glycol and/or glycerol, 0.5-1.5 wt % salt selected from sodium chloride, potassium chloride, magnesium chloride, calcium chloride and combinations thereof, and at least 30 wt % water.

17. The wound dressing of claim 16 wherein the prepolymer having aliphatic diisocyanate groups includes isophorone diisocyanate.

18. The wound dressing of claim 1, wherein the hydrophilic polyurethane foam has a water content of at least 35 wt % of water and at most 65 wt % of water.

19. The wound dressing of claim 1 wherein the transition layer forms an adhesive bond between the first layer and the second layer.

20. The wound dressing of claim 1 wherein the polyurethane foam is capable of rereleasing at least some of the water present in the polyurethane foam.

21. The wound dressing of claim 1 wherein the wound dressing has a smaller shearing stress on a wound than an identical wound dressing comprising a dry hydrophilic polyurethane foam.

22. The wound dressing of claim 1 wherein the wound dressing has a smaller shearing stress on further plies or materials and a smaller shearing stress on a wound than an identical wound dressing comprising a dry hydrophilic polyurethane foam.

23. A laminate dressing consisting essentially of:
a) a first layer as a wound contact layer having a first side and a second side, and a multiplicity of channels, and including a hydrogel matrix which comprises a polyurethane-polyurea copolymer formed from a prepolymer having aliphatic diisocyanate groups and a polyamine based on polyethylene oxide, and wherein the hydrogel matrix contains from 20% to 80% of wound deliverable water;
b) at least one second layer as an absorbent layer having a first side and a second side and comprising a hydrophilic polyurethane foam which has a water fraction of at least 10% by weight and at most 80% by weight of water, a free absorbency $A_2$ of at least 10 g/g determined by DIN-EN13726-1 and a swell capacity $\Delta V_1$ of at most 60%; and, c) a transition layer disposed between the first layer and the second layer and which transition layer consists of a portion of the hydrogel matrix of the first layer which has penetrated into a portion of the polyurethane foam of the second layer, said transition layer having channels which are filled with only polyurethane foam from the second side of the second layer and which channels are disposed congruent relative to the channels in the hydrogel matrix of the first layer.

24. The laminate of claim 23 wherein the transition layer forms an adhesive bond between the first layer and the second layer.

25. The laminate of claim 23 wherein the polyurethane foam is capable of rereleasing at least some of the water present in the polyurethane foam.

26. The laminate of claim 23 wherein the laminate has a smaller shearing stress on a wound than an identical laminate comprising a dry hydrophilic polyurethane foam.

27. The laminate of claim 23 wherein the laminate has a smaller shearing stress on further plies or materials and a smaller shearing stress on a wound than an identical laminate comprising a dry hydrophilic polyurethane foam.

\* \* \* \* \*